United States Patent
Gusmeroli et al.

(10) Patent No.: US 7,166,620 B2
(45) Date of Patent: Jan. 23, 2007

(54) THIAZOLE DERIVATIVES WITH FUNGICIDAL ACTIVITY

(75) Inventors: Marilena Gusmeroli, Monza-Milan (IT); Alessandro Ciapessoni, Pavia (IT); Franco Bettarini, Novara (IT); Samuele Osti, Usmate-Velate-Milan (IT); Luigi Mirenna, Milan (IT); Giovanni Camaggi, Novara (IT); Alexia Elmini, Buronzo-Vercelli (IT); Ramona Gironda, Lumellogno-Novara (IT)

(73) Assignee: Isagro Ricerca S.r.l., Milan (IT)

( * ) Notice: Subject to any disclaimer, the term of this patent is extended or adjusted under 35 U.S.C. 154(b) by 0 days.

(21) Appl. No.: 10/497,611

(22) PCT Filed: Dec. 11, 2002

(86) PCT No.: PCT/EP02/14070

§ 371 (c)(1),
(2), (4) Date: Nov. 12, 2004

(87) PCT Pub. No.: WO03/050096

PCT Pub. Date: Jun. 19, 2003

(65) Prior Publication Data

US 2005/0065197 A1    Mar. 24, 2005

(30) Foreign Application Priority Data

Dec. 13, 2001 (IT) ............ MI2001A2640
Apr. 9, 2002 (IT) ............ MI2002A0753

(51) Int. Cl.
*A01N 43/40* (2006.01)
*A01N 43/78* (2006.01)
*C07D 277/34* (2006.01)
*C07D 417/04* (2006.01)

(52) U.S. Cl. ............ 514/342; 514/369; 546/270.4; 548/187

(58) Field of Classification Search ............ None
See application file for complete search history.

(56) References Cited

U.S. PATENT DOCUMENTS 6,031,110 A * 2/2000 Kirstgen et al. ......... 548/370.1

FOREIGN PATENT DOCUMENTS

WO    WO 93/08180    4/1993

* cited by examiner

*Primary Examiner*—Kamal A. Saeed
*Assistant Examiner*—Andrew B. Freistein
(74) *Attorney, Agent, or Firm*—Hedman & Costigan, P.C.; James V. Costigan

(57) ABSTRACT

Compounds having general formula (I) are described, together with their use for the control of phytopathogenic fungi

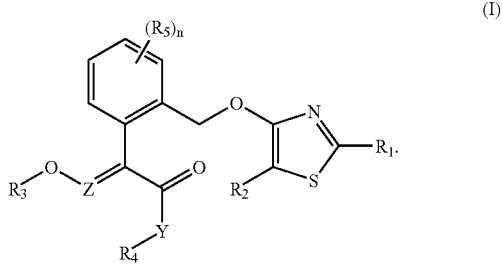

13 Claims, No Drawings

THIAZOLE DERIVATIVES WITH FUNGICIDAL ACTIVITY

This application is filed pursuant to 35 U.S.C. § 371 as a United States National Phase Application of International Application No. PCT/EP02/14070, filed on Dec. 11, 2002.

The present invention relates to new thiazole derivatives.

More specifically, the present invention relates to new thiazole derivatives having high fungicidal activity, the process for their preparation, and their use for the control of phytopathogenic fungi, in particular in the agrarian field.

Strobilurines are fungal metabolites chemically characterized by the presence of the group 1-methoxycarbonyl-2-methoxyethen-1-yl ("Pesticide Science", 1991, page 499).

They mainly act as inhibitors of mitochondrial respiration and have shown good control of the myceliar growth of various fungal species in tests in vitro.

The presence of dienic or trienic systems in the molecular skeleton, however, makes these compounds unsuitable for practical use due to the high photochemical instability.

The use of the thiazol-2-yl group in analogous products of strobilurines, having a good fungicidal activity with respect to phytopathogenic fungi, as described in patent application WO 9940076, is known in literature.

The Applicant has now found new analogous products of strobilurines, chemically characterized by the presence of a 4-thiazole group, having a good stability and surprisingly high fungicidal activity with respect to phytopathogenic fungi, together with a good selectivity towards the vegetables to which they are applied.

The object of the present invention therefore relates to compounds having general formula (I):

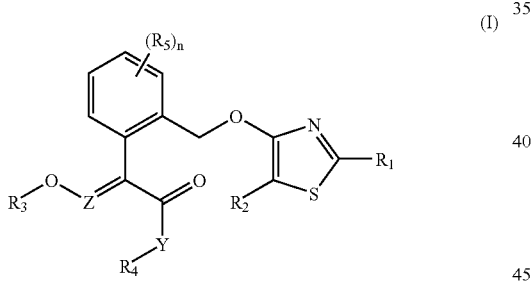

wherein:
$R_1$ represents a hydrogen atom; a linear or branched $C_1$–$C_6$ alkyl or haloalkyl group, optionally substituted; a $C_2$–$C_6$ alkenyl or haloalkenyl group, optionally substituted; a $C_2$–$C_6$ alkynyl or haloalkynyl group, optionally substituted; a $C_3$–$C_6$ cycloalkyl group, optionally substituted; an aryl group, optionally substituted; a heteroaryl group, optionally substituted; a heterocyclic group, optionally substituted; a halogen atom;

$R_2$ represents a hydrogen atom; a halogen atom selected from chlorine, fluorine, bromine or iodine; a linear or branched $C_1$–$C_6$ alkyl or haloalkyl group, optionally substituted; a linear or branched $C_2$–$C_6$ alkenyl or haloalkenyl group, optionally substituted; a linear or branched $C_2$–$C_6$ alkynyl or haloalkynyl group, optionally substituted; a $C_3$–$C_6$ cycloalkyl group, optionally substituted; a linear or branched $C_1$–$C_6$ alkoxy or haloalkoxy group, optionally substituted; a linear or branched $C_1$–$C_6$ alkylthio or haloalkylthio group, optionally substituted; a $C_3$–$C_6$ cycloalkoxy group, optionally substituted; a cyano group; a linear or branched $C_2$–$C_8$ alkoxycarbonyl group, optionally substituted; an aminocarbonyl group; a linear or branched $C_2$–$C_8$ alkylaminocarbonyl group; a linear or branched $C_3$–$C_{15}$ dialkylaminocarbonyl group; a linear or branched $C_2$–$C_8$ alkylcarbonyl group, optionally substituted; an aryl group, optionally substituted or a heteroaryl group, optionally substituted; a heterocyclic group, optionally substituted;

$R_3$ and $R_4$ independently represent a linear or branched $C_1$–$C_4$ alkyl group;

$R_5$, the same or different when n is greater than or equal to 2, represents a halogen atom, optionally selected from fluorine, chlorine, bromine or iodine; a linear or branched $C_1$–$C_6$ haloalkyl group, optionally substituted; a linear or branched $C_1$–$C_6$ alkoxy group, optionally substituted; a linear or branched $C_1$–$C_6$ haloalkoxy group, optionally substituted; a linear or branched $C_1$–$C_6$ alkylthio group, optionally substituted; a linear or branched $C_1$–$C_6$ haloalkylthio group, optionally substituted; a $C_3$–$C_6$ cycloalkyl group optionally substituted; a linear or branched $C_2$–$C_8$ alkoxycarbonyl group; a cyano group; when $R_1$ represents a linear or branched $C_1$–$C_6$ haloalkyl group, substituted by at least two halogen atoms, the same or different, i.e. a linear or branched $C_1$–$C_6$ polyhaloalkyl group, $R_5$ also represents a linear or branched $C_1$–$C_6$ alkyl group, optionally substituted;

Y represents an oxygen atom; an NH group;

Z represents a nitrogen atom or a CH group;

n is a number ranging from 0 to 4.

A further object of the present invention relates to the use of the compounds having general formula (I):

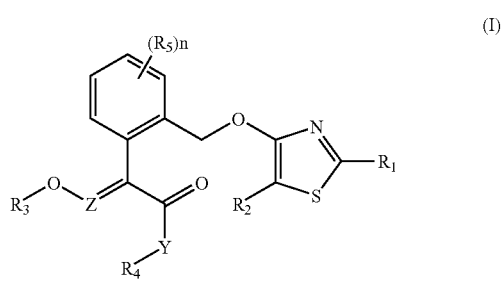

wherein:
$R_1$ represents a hydrogen atom; a linear or branched $C_1$–$C_6$ alkyl or haloalkyl group, optionally substituted; a $C_2$–$C_6$ alkenyl or haloalkenyl group, optionally substituted; a $C_2$–$C_6$ alkynyl or haloalkynyl group, optionally substituted; a $C_3$–$C_6$ cycloalkyl group, optionally substituted; an aryl group, optionally substituted; a heteroaryl group, optionally substituted; a heterocyclic group, optionally substituted; a halogen atom;

$R_2$ represents a hydrogen atom; a halogen atom selected from chlorine, fluorine, bromine or iodine; a linear or branched $C_1$–$C_6$ alkyl or haloalkyl group, optionally substituted; a linear or branched $C_2$–$C_6$ alkenyl or haloalkenyl group, obtionally substituted; a linear or branched $C_2$–$C_6$ alkynyl or haloalkynyl group, optionally substituted; a $C_3$–$C_6$ cycloalkyl group, optionally substituted; a linear or branched $C_1$–$C_6$ alkoxy or haloalkoxy group, optionally substituted; a linear or branched $C_1$–$C_6$ alkylthio or haloalkylthio group, optionally substituted; a $C_3$–$C_6$ cycloalkoxy group, optionally substituted; a cyano group; a linear or branched $C_2$–$C_8$ alkoxycarbonyl group, optionally substituted; an aminocarbonyl group; a linear or branched $C_2$–$C_8$ alkylaminocarbonyl group; a linear or branched $C_3$–$C_{15}$ dialkylaminocarbonyl group; a linear or branched $C_2$–$C_8$ alkylcarbonyl group, optionally substituted; an aryl group, optionally substituted, or heteroaryl group, optionally substituted; a heterocyclic group, optionally substituted;

$R_3$ and $R_4$ independently represent a linear or branched $C_1$–$C_4$ alkyl group;

$R_5$, the same or different when n is greater than or equal to 2, represents a halogen atom, optionally selected from fluorine, chlorine, bromine or iodine; a linear or branched $C_1$–$C_6$ haloalkyl group, optionally substituted; a linear or branched $C_1$–$C_6$ alkoxy group, optionally substituted; a linear or branched $C_1$–$C_6$ haloalkoxy group, optionally substituted; a linear or branched $C_1$–$C_6$ alkylthio group, optionally substituted; a linear or branched $C_1$–$C_6$ haloalkylthio group, optionally substituted; a $C_3$–$C_6$ cycloalkyl group, optionally substituted; a linear or branched $C_2$–$C_8$ alkoxycarbonyl group; a cyano group; when $R_1$ represents a linear or branched $C_1$–$C_6$ haloalkyl group substituted by at least two halogen atoms, the same or different, i.e. a linear or branched $C_1$–$C_6$ polyhaloalkyl group, $R_5$ also represents a linear or branched $C_1$–$C_6$ alkyl group, optionally substituted;

Y represents an oxygen atom; an NH group;

Z represents a nitrogen atom or a CH group;

n is a number ranging from 0 to 4, for the control of phytopathogenic fungi.

In particular, the use of the compounds having formula (I) for the control of phytopathogenic fungi is curative and/or preventive.

In the compounds having formula (I), the $R_1$ group is preferably selected from a linear or branched $C_1$–$C_6$ alkyl or haloalkyl group, optionally substituted; a $C_3$–$C_6$ cycloalkyl group, optionally substituted; an aryl group, optionally substituted; a heteroaryl group, optionally substituted.

The $R_2$ group is preferably selected from a hydrogen atom; a halogen atom; a linear or branched $C_1$–$C_6$ alkyl or haloalkyl group, optionally substituted; a $C_3$–$C_6$ cycloalkyl group, optionally substituted; a linear or branched $C_2$–$C_8$ alkoxycarbonyl group, optionally substituted.

$R_3$ and $R_4$ are preferably equal to a methyl group, whereas $R_5$ is preferably selected from a halogen atom, a $C_1$–$C_6$ haloalkyl group or, when $R_1$ represents a $C_1$–$C_6$ haloalkyl group, $R_5$ preferably represents a linear or branched $C_1$–$C_6$ alkyl group, optionally substituted.

n is preferably equal to 0 or 1, whereas Z is preferably equal to CH and Y is preferably an oxygen atom.

A $C_1$–$C_6$ alkyl group refers to a linear or branched $C_1$–$C_6$ alkyl group.

Examples of this group are: methyl, ethyl propyl, isopropyl, butyl, isobutyl, tert-butyl.

A $C_1$–$C_6$ haloalkyl group refers to a linear or branched alkyl group substituted by one or more halogen atoms, the same or different. In particular, a polyhaloalkyl group refers to a haloalkyl group substituted by at least two halogen atoms, the same or different.

Examples of this group are: fluoromethyl, chlorodifluoromethyl, difluoromethyl, trifluoromethyl, trichloromethyl, 2,2,2-trifluoroethyl, 2,2,2-trichloroethyl, 1,1,2,2,2-pentafluoroethyl, 1,1,2,2-tetrafluoroethyl, 1,2,2,2-tetrafluoroethyl, 2,2,3,3-tetrafluoropropyl, 2,2,3,3,3-pentafluoropropyl.

A $C_2$–$C_6$ alkenyl group refers to a linear or branched $C_2$–$C_6$ alkenyl group.

Examples of this group are: ethenyl, propenyl, butenyl.

A $C_2$–$C_6$ haloalkenyl group refers to a linear or branched $C_2$–$C_6$ alkenyl group, substituted by one or more halogen atoms, the same or different.

Examples of this group are: 2,2-dichloropropenyl, 1,2,2-trichloropropenyl.

Examples of $C_2$–$C_6$ alkynyl groups are: ethynyl, propargyl.

A $C_2$–$C_6$ haloalkynyl group refers to a $C_2$–$C_6$ alkynyl group substituted by one or more halogen atoms, the same or different.

An example of a $C_2$–$C_6$ haloalkynyl group is: 3-chloropropynyl.

A $C_3$–$C_6$ cycloalkyl group refers to a cycloalkyl group whose ring consists of 3–6 carbon atoms, optionally substituted by one or more substituents, the same or different.

Examples of this group are: cyclopropyl, cyclobutyl, cyclopentyl, cyclohexyl.

A $C_1$–$C_6$ alkoxy group refers to a $C_1$–$C_6$ alkoxy group, wherein the aliphatic portion is a $C_1$–$C_6$ alkyl group, as defined above.

Examples of this group are: methoxy, ethoxy.

A $C_1$–$C_6$ haloalkoxy group refers to a $C_1$–$C_6$ haloalkoxy group, wherein the aliphatic portion is a $C_1$–$C_6$ haloalkyl group, as defined above.

Examples of this group are: trifluoromethoxy, 1,1,2,2-tetrafluoroethoxy, 1,1,2,3,3,3-hexafluoropropyloxy.

A $C_1$–$C_6$ alkylthio group refers to a $C_1$–$C_6$ alkylthio group, wherein the aliphatic portion is a $C_1$–$C_6$ alkyl group, as defined above.

Examples of this group are: methylthio, ethylthio.

A $C_1$–$C_6$ haloalkylthio group refers to a $C_1$–$C_6$ haloalkylthio group wherein the aliphatic portion is a $C_1$–$C_6$ haloalkyl group, as defined above.

Examples of this group are: trifluoromethylthio, 1,1,2,2-tetrafluoroethylthio.

A $C_3$–$C_6$ cycloalkoxy group refers to a $C_3$–$C_6$ cycloalkoxy group wherein the aliphatic portion is a $C_3$–$C_6$ cycloalkyl group, as defined above.

Examples of this group are: cyclopentoxy, cyclohexyloxy.

A $C_2$–$C_6$ alkoxycarbonyl group refers to an alkoxycarbonyl group wherein the aliphatic portion is a $C_1$–$C_7$ alkyl group, as defined above.

Examples of this group are: methoxycarbonyl, ethoxycarbonyl, propoxycarbonyl.

A $C_2$–$C_8$ alkylaminocarbonyl or $C_3$–$C_{15}$ dialkylaminocarbonyl group refers to an alkylaminocarbonyl or dialkylaminocarbonyl group wherein the aliphatic portion is one or two $C_1$–$C_7$ alkyl groups respectively, as defined above.

Examples of this group are: N-methylaminocarbonyl, N,N-dimethylaminocarbonyl, N-isopropylaminocarbonyl, N-ethyl-N-methylaminocarbonyl.

A $C_2$–$C_8$ alkylcarbonyl group refers to an alkylcarbonyl group wherein the aliphatic portion is a $C_1$–$C_7$ alkyl group, as defined above.

Examples of this group are: methylcarbonyl, ethylcarbonyl, isopropylcarbonyl.

An aryl group refers to an aromatic carbocyclic group optionally substituted by one or more groups the same or different.

Examples of this group are: phenyl, naphthyl.

A heteroaryl group refers to an aromatic heterocyclic penta- or hexa-atomic group, also benzocondensed or heterobicyclic, containing from 1 to 4 hetero-atoms selected from nitrogen, oxygen, sulfur, optionally substituted by one or more groups, the same or different.

Examples of heteroaryl groups are: pyridine, pyrimidine, pyridazine, pyrazine, triazine, tetrazine, quinoline, quinoxaline, quinazoline, furan, thiophene, pyrrole, oxazole, thiazole, isoxazole, isothiazole, oxadiazole, thiadiazole, pyrazole, imidazole, triazole, tetrazole, indole, benzofurane, benzothiophene, benzoxazole, benzothiazole, benzoxadiazole, benzothiadiazole, benzopyrazole, benzimidazole, benzotriazole, triazolopyridine, triazolopyrimidine, thiazolotriazole.

A heterocyclic group refers to a saturated or unsaturated ring with from three to twelve units, containing at least one hetero-atom selected from nitrogen, oxygen, sulfur, optionally condensed with another aromatic or non-aromatic ring.

Examples of heterocyclic rings are: pyrrolidine, piperidine, dihydropiperidine, dihydropyridine, piperazine, morpholine, thiazine, indoline.

In the present invention, the term optionally or possibly substituted refers to a group which can have one or more substituents, the same or different, preferably selected from the following groups: halogen atoms possibly selected from chlorine, fluorine, bromine, iodine; $C_1$–$C_6$ alkyl, alkoxy, alkylthio, in turn optionally substituted by halogen atoms; alkoxycarbonyl or alkylaminocarbonyl optionally halogenated; aminocarbonyl; $C_2$–$C_8$ dialkylaminocarbonyl optionally halogenated; $C_2$–$C_8$ alkylcarbonyl; $C_2$–$C_8$ alkylcarbonyloxy; cyano; nitro; formyl; hydroxy; amino; carboxy.

As already mentioned, the compounds having formula (I) have high fungicidal activity.

Examples of compounds having formula (I) which are interesting for their activity are:

methyl (E)-3-methoxy-2-{2-[2-(trifluoromethyl)-5-methylthiazol-4-yloxymethyl]phenyl}acrylate;
methyl (E)-2-methoxyimino-2-{2-[2-(trifluoromethyl)-5-methylthiazol-4-yloxymethyl]phenyl}-acetate;
N-methyl-(E)-2-methoxyimino-2-{2-[2-(trifluoromethyl)-5-methylthiazol-4-yloxymethyl]phenyl}-acetamide;
methyl (E)-3-methoxy-2-{2-[2-(1,1,2,2,2-pentafluoroethyl)-5-methylthiazol-4-yloxymethyl]-phenyl}acrylate;
N-methyl-(E)-2-methoxyimino-2-{2-[2-(1,1,2,2,2-pentafluoroethyl)-5-methylthiazol-4-yloxymethylphenyl}acetamide;
methyl (E)-3-methoxy-2-{2-[2-(1,1,2,2-tetrafluoroethyl)-5-methylthiazol-4-yloxymethyl]-phenyl}acrylate;
methyl (E)-2-methoxyimino-2-{2-[2-(1,1,2,2,2-pentafluoro-ethyl)-5-methylthiazol-4-yloxymethyl]-phenyl}acetate;
methyl (E)-3-methoxy-2-{2-[2-(1,2,2,2-tetrafluoroethyl)-5-methylthiazol-4-yloxymethyl]phenyl}-acrylate;
N-methyl-(E)-2-methoxyimino-2-{2-[2-(1,1,2,2-tetrafluoroethyl)thiazol-4-yloxymethyl]phenyl}-acetamide;
methyl (E)-3-methoxy-2-{2-[2-(2,2,2-trifluoroethyl)-5-methylthiazol-4-yloxymethyl]phenyl}-acrylate;
methyl (E)-2-methoxyimino-2-{2-[2-(1,1,2,2-tetrafluoroethyl)-5-methylthiazol-4-yloxymethyl]-phenyl}acetate;
N-methyl-(E)-2-methoxyimino-2-{2-[2-(1,2,2,2-tetrafluoroethyl)-5-methyl-thiazol-4-yloxymethyl]phenyl}acetamide;
methyl (E)-3-methoxy-2-{2-[2-(trifluoromethyl)thiazol-4-yloxymethyl]phenyl}acrylate;
methyl (E)-3-methoxy-2-{2-[2-(trifluoromethyl)-5-chlorothiazol-4-yloxymethyl]phenyl}acrylate;
N-methyl-(E)-2-methoxyimino-2-{2-[2-(2,2,2-trifluoroethyl)-5-methyl-thiazol-4-yloxymethyl]phenyl}acetamide;
N-methyl-(E)-2-methoxyimino-2-{2-[2-(trifluoromethyl)-5-ethylthiazol-4-yloxymethyl]-phenyl}acetamide;
methyl (E)-2-methoxyimino-2-{2-[2-(1,2,2,2-tetrafluoroethyl)-5-methylthiazol-4-yloxymethyl]-phenyl}acetate;
methyl (E)-2-methoxyimino-2-{2-[2-(2,2,2-trifluoroethyl)-5-methylthiazol-4-yloxymethyl]-phenyl}acetate;
methyl (E)-3-methoxy-2-{2-[2-(trifluoromethyl)-5-ethylthiazol-4-yloxymethyl]phenyl}acrylate;
methyl (E)-3-metoxy-2-{2-[2-(trifluoromethyl)-5-cyclopropylthiazol-4-yloxymethyl]phenyl}acrylate;
methyl (E)-3-methoxy-2-{2-[2-(difluoromethyl)-5-methylthiazol-4-yloxymethyl]phenyl}acrylate;
N-methyl-(E)-2-methoxyimino-2-{2-[2-(difluoromethyl)-5-methylthiazol-4-yloxymethyl]phenyl}acetamide;
methyl (E)-3-methoxy-2-{2-[2-(chlorodifluoromethyl)-5-methylthiazol-4-yloxymethyl]phenyl}-acrylate;
N-methyl-(E)-2-methoxyimino-2-{2-[2-(chlorodifluoromethyl)-5-methylthiazol-4-yloxymethyl]-phenyl}acetamide;
methyl (E)-3-methoxy-2-[2-(2-(pyridin-2-yl)-5-methylthiazol-4-yloxymethyl)phenyl]acrylate;
methyl (E)-2-metoxyimino-2-[2-(2-(pyridin-2-yl)-5-methylthiazol-4-yloxymethyl)phenyl]acetate;
N-methyl-(E)-2-methoxyimino-2-[2-(2-(pyridin-2-yl)-5-methylthiazol-4-yloxymethyl) phenyl]acetamide;
methyl (E)-3-methoxy-2-[2-(2-(pyridin-3-yl)-5-methylthiazol-4-yloxymethyl)phenyl]acrylate;
N-methyl-(E)-2-methoxyimino-2-[2-(2-(pyridin-3-yl)-5-methylthiazol-4-yloxymethyl) phenyl]-acetamide;
methyl (E)-3-methoxy-2-[2-(2-(pyridin-4-yl)-5-methylthiazol-4-yloxymethyl)phenyl]acrylate;
N-methyl-(E)-2-methoxyimino-2-[2-(2-(pyridin-4-yl)-5-methylthiazol-4-yloxymethyl) phenyl]-acetamide;
methyl (E)-3-methoxy-2-[2-(2-(4-chlorophenyl)-5-methylthiazol-4-yloxymethyl)phenyl]acrylate;
N-methyl-(E)-2-methoxyimino-2-[2-(2-(2, 6-difluorophenyl)thiazol-4-yloxymethyl) phenyl]-acetamide;
methyl (E)-3-methoxy-2-[2-(2-cyclopropyl-5-methylthiazol-4-yloxymethyl)phenyl]acrylate;
methyl (E)-2-methoxyimino-2-[2-(2-(2-fluorophenyl)-5-methylthiazol-4-yloxymethyl)-phenyl]-acetate;
N-methyl-(E)-2-methoxyimino-2-[2-(2-(2-propyl)-5-methylthiazol-4-yloxymethyl) phenyl]acetamide;
methyl (E)-3-methoxy-2-[2-(2-(pyridin-2-yl)-thiazol-4-yloxymethyl)phenyl]acrylate;
methyl (E)-3-methoxy-2-[2-(2-(pyridin-2-yl)-5-trifluoromethylthiazol-4-yloxymethyl)phenyl]-acrylate;
N-methyl-(E)-2-methoxyimino-2-[2-(2-phenyl-5-(methoxycarbonyl)thiazol-4-yloxymethyl)phenyl]-acetamide;
N-methyl-(E)-2-methoxyimino-2-[2-(2-(4-methylphenyl)-5-cyano-thiazol-4-yloxymethyl)phenyl]-acetamide;
methyl (E)-3-methoxy-2-[2-(2-(4-trifluoromethylphenyl)-5-cyclopropylthiazol-4-yloxymethyl)phenyl]acrylate;
methyl (E)-3-methoxy-2-[2-(2-(2,4-dichlorophenyl)-5-methoxythiazol-4-yloxymethyl)phenyl]acrylate.

A further object of the present invention relates to the processes for the preparation of the compounds having general formula (I).

The compounds having general formula (I) can be obtained by the condensation of a compound having general formula (II) with a thiazolyl derivative having general formula (III), according to reaction scheme A:

Scheme A

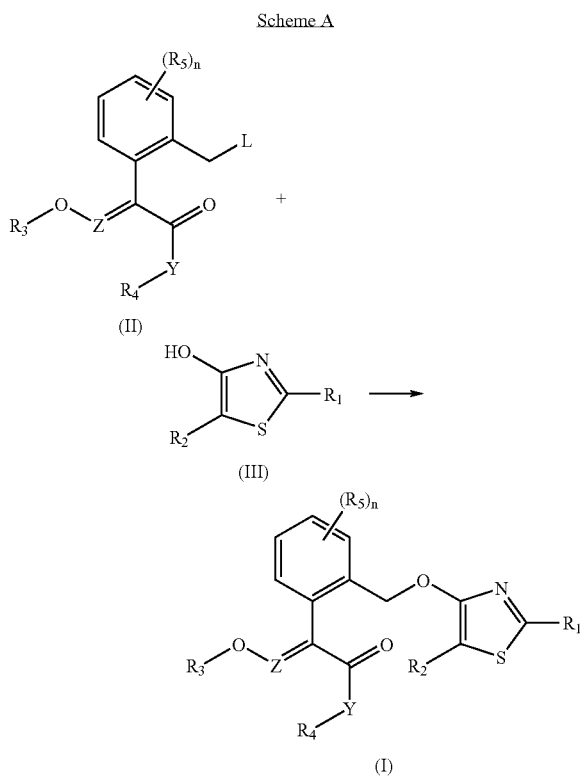

wherein $R_1$, $R_2$, $R_3$, $R_4$, $R_5$, Y, Z and n have the meanings defined above, L represents a leaving group such as a chlorine atom, a bromine atom, an $RSO_3^-$ group wherein R represents a $C_1-C_6$ alkyl or haloalkyl or a phenyl optionally substituted.

The reaction can be conveniently carried out in an inert organic solvent, at a temperature ranging from 0° C. to the boiling point of the reaction mixture, optionally in the presence of an inorganic or organic base.

Preferred solvents for the reaction are: alcohols (methanol, ethanol, propanol, methoxyethanol etc.); ethers (ethyl ether, isopropyl ether, tetrahydrofuran, dioxane, dimethoxyethane, etc.); esters (ethyl acetate, etc.); ketones (acetone, methylethylketone etc.); chlorinated hydrocarbons (methylene chloride, dichloroethane, chloroform, carbon tetrachloride, etc.); aromatic hydrocarbons (benzene, toluene, xylene, etc.); aliphatic hydrocarbons (hexane, heptane, cyclohexane, etc.); dipolar aprotic solvents (N,N-dimethylformamide, dimethylsulfoxide, sulfolane, etc.).

Preferred inorganic bases are: hydrides, hydroxides, carbonates of alkaline or earth-alkaline metals (sodium, potassium, calcium, etc.).

Preferred organic bases are: pyridine, dimethylaminopyridine, aliphatic amines, (diethylamine, triethylamine, etc.), cyclic amines (morpholine, piperidine, diazabicycloundecene, etc.); alcoholates of alkaline metals (potassium t-butylato, etc.).

The compounds having general formula (I), wherein Z is N and Y is NH, can be alternatively obtained by the reaction of the corresponding compound having formula (I) wherein Z is N and Y is O with a suitable amine having the formula $R_4NH_2$ wherein $R_4$ has the meanings defined above.

The reaction can be conveniently carried out in an inert organic solvent, at a temperature ranging from 0° C. to the boiling point of the reaction mixture.

Preferred solvents for the reaction are: alcohols (methanol, ethanol, propanol, methoxyethanol, etc.); ethers (ethyl ether, isopropyl ether, tetrahydrofuran, dioxane, dimethoxyethane, etc.); ketones (acetone methylethylketone etc.); chlorinated hydrocarbons (methylene chloride, dichloroethane, chloroform, carbon tetrachloride etc.); aromatic hydrocarbons (benzene, toluene, xylene, etc.); aliphatic hydrocarbons (hexane, heptane cyclohexane, etc.); dipolar aprotic solvents (N,N-dimethylformamide, dimethylsulfoxide, sulfolane, etc.); or mixtures of these in any ratio.

The compounds having general formula (I) have isomerism on the double bond $R_4YCO-C=Z-OR_3$; the object of the present invention also includes the use of the compounds having formula (I) as isomeric mixtures in any proportion, and also the formation and use of the single isomers E or Z of the compounds having formula (I). For the purposes of the fungicidal activity, however, isomers E of the compounds having formula (I) are preferred, and consequently the use of isomers E of the compounds having formula (I), is also preferred.

The intermediates having general formula (II) are known compounds.

The thiazoles having general formula (III), when not known as such, can be prepared by means of the methods known in literature, according to what is described, for example, in: Journal of Medicinal Chemistry 1991, vol. 34, pages 2158–2165.

The thiazoles having general formula (III) wherein $R_1$ has the meaning of a linear or branched $C_1-C_6$ polyhaloalkyl group are new compounds.

A further object of the present invention therefore relates to compounds having general formula (III'):

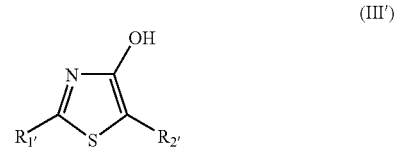

wherein $R_1'$ represents a linear or branched $C_1-C_6$ polyhaloalkyl group and $R_2'$ has the same meaning as $R_2$ and their use as intermediates for the preparation of compounds useful both in the agrochemical and pharmaceutical field.

A $C_1-C_6$ polyhaloalkyl group refers to a linear or branched $C_1-C_6$ alkyl group substituted by at least two halogen atoms, the same or different.

In particular, the group $R_1'$ is selected from trifluoromethyl, difluoromethyl, chlorodifluoromethyl, 2,2,2-trifluoroethyl, 2,2,3,3-tetrafluoropropyl, 2,2,3,3,3-pentafluoropropyl, 1,1,2,2,2-pentafluoroethyl, 1,2,2,2-tetrafluoroethyl, 1,1,2,2-tetrafluoroethyl.

The group $R_2'$ is preferably selected from a hydrogen atom, a halogen atom, a linear or branched $C_1-C_6$ alkyl or haloalkyl group, optionally substituted, a $C_3-C_6$ cycloalkyl group, optionally substituted; an aryl group, optionally substituted; a heteroaryl group, optionally substituted; a cyano group; a linear or branched $C_2-C_8$ alkoxycarbonyl group, optionally substituted.

The compounds having formula (III') can also exist in a tautomeric ketonic form (IV), and also in mixtures between the two forms (III') e (IV).

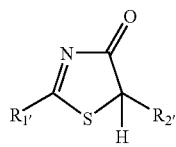

(IV)

Examples of the intermediates having formula (III') of particular interest are:
2-(trifluoromethyl)-4-hydroxy-5-methylthiazole;
2-(trifluoromethyl)-4-hydroxy-5-chlorothiazole;
2-(trifluoromethyl)-4-hydroxythiazole;
2-(trifluoromethyl)-4-hydroxy-5-cyclopropylthiazole;
2-(trifluoromethyl)-4-hydroxy-5-(2-pyridyl)thiazole;
2-(trifluoromethyl)-4-hydroxy-5-(dichlorophenyl)thiazole;
2-(trifluoromethyl)-4-hydroxy-5-cyanothiazole;
2-(1,1,2,2,2-pentafluoroethyl)-4-hydroxy-5-methylthiazole;
2-(1,1,2,2,2-pentafluoroethyl)-4-hydroxy-5-phenylthiazole;
2-(1,1,2,2,2-pentafluoroethyl)-4-hydroxythiazole;
2-(2,2,2-trifluoroethyl)-4-hydroxy-5-methylthiazole;
2-(2,2,2-trifluoroethyl)-4-hydroxythiazole;
2-(1,2,2,2-tetrafluoroethyl)-4-hydroxy-5-methylthiazole;
2-(1,2,2,2-tetrafluoroethyl)-4-hydroxythiazole;
2-(1,1,2,2-tetrafluoroethyl)-4-hydroxy-5-methylthiazole;
2-(1,1,2,2-tetrafluoroethyl)-4-hydroxy-5-phenylthiazole;
2-(1,1,2,2-tetrafluoroethyl)-4-hydroxythiazole;
2-(difluoromethyl)-4-hydroxy-5-methylthiazole;
2-(difluoromethyl)-4-hydroxythiazole;
2-(difluoromethyl)-4-hydroxy-5-cyclopentylthiazole;
2-(chlorodifluoromethyl)-4-hydroxy-5-methylthiazole;
2-(chlorodifluoromethyl)-4-hydroxythiazole;
2-(trifluoromethyl)-4-hydroxy-5-phenylthiazole;
2-(trifluoromethyl)-4-hydroxy-5-ethoxycarbonylthiazole.

It is also known from the chemical literature relating to 4-hydroxythiazoles that in polar solvents such as dimethylsulfoxide, N,N-dimethylformamide, the prevalent form is hydroxylic (III'), according to what is described, for example, in: Comprehensive Heterocyclic Chemistry, vol. 6, pages 248–249.

A further object of the present invention relates to the processes for the preparation of the compounds having general formula (III').

The compounds having general formula (III') can be obtained by the condensation of a thioamide having formula (V) with a derivative having formula (VI), according to reaction scheme B:

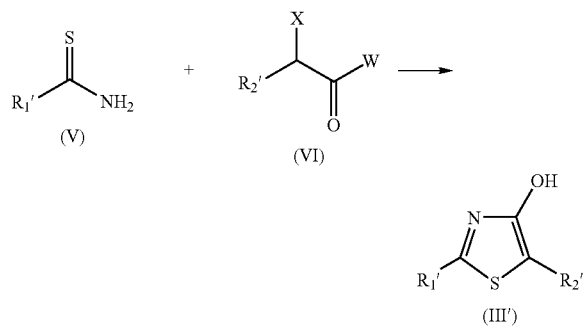

wherein $R_1'$ and $R_2'$ have the meanings defined above, X represents a leaving group such as a chlorine atom, a bromine atom, a $RSO_3^-$ group, W represents an OR group, wherein R has the meaning of a linear or branched $C_1$–$C_6$ alkyl or haloalkyl or phenyl, optionally substituted; or a halogen atom; or an $NH_2$ group.

The reaction can be conveniently carried out in an inert organic solvent, at a temperature ranging from –70° C. to the boiling point of the reaction mixture, optionally in the presence of an inorganic or organic base.

Preferred solvents for the reaction are: aromatic hydrocarbons (benzene, toluene, xylene, etc.); aliphatic hydrocarbons (hexane, heptane, cyclohexane, etc.); alcohols (methanol, ethanol, etc.); ethers (ethyl ether, isopropyl ether, tetrahydrofuran, dioxane, dimethoxyethane, etc.); esters (ethyl acetate, etc.); ketones (acetone, methylethylketone, etc.); chlorinated hydrocarbons (methylene chloride, dichloroethane, chloroform, carbon tetrachloride, etc.); dipolar aprotic solvents (N,N-dimethylformamide, dimethylsulfoxide, sulfolane, etc.).

Preferred inorganic bases are: hydrides, hydroxides, carbonates of alkaline and earth-alkaline metals (sodium, potassium, calcium, etc.).

Preferred organic bases are: pyridine, dimethylaminopyridine, aliphatic amines, (diethylamine, triethylamine, etc.), cyclic amines (morpholine, piperidine, diazabicycloundecene, etc.); alcoholates of alkaline metals (potassium t-butylate, etc.).

The thioamides having general formula (V), when they are not known as such, can be prepared by means of the methods known in literature, according to what is described, for example, in: Houben-Weil Band E5/Teil 1 (pages 1218–1277).

The intermediates having general formula (VI) are compounds known in literature, for example, in: Journal American Chemical Society (1944), vol. 66, page 2074; Synthesis (1969), page 39.

Alternatively, the compounds having general formula (III') can be obtained by condensation between a nitrile having formula (VII) and a carboxylic derivative having formula (VIII) according to reaction scheme C:

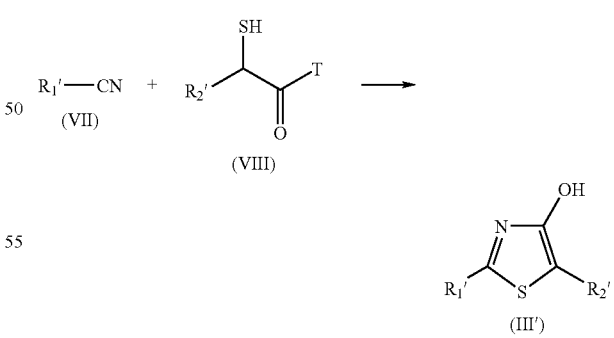

wherein $R_1'$ and $R_2'$ have the meanings defined above, T represents an OH group or an OR group wherein R has the meaning of a linear or branched $C_1$–$C_6$ alkyl or haloalkyl, or phenyl optionally substituted.

The reaction can be conveniently carried out in the presence of or in the absence of an inert organic solvent, at a temperature ranging from –70° C. to the boiling point of the reaction mixture, optionally in the presence of an inorganic or organic base or alternatively in the presence of an inorganic or organic acid.

Preferred solvents for the reaction are: aromatic hydrocarbons (benzene, toluene, xylene, etc.); aliphatic hydrocarbons (hexane, heptane, cyclohexane, etc.); alcohols (methanol, ethanol, ecc.); ethers (ethyl ether, isopropyl ether, tetrahydrofuran, dioxane, dimethoxyethane, etc.); esters (ethyl acetate, etc.); ketones (acetone, methylethylketone, etc.); chlorinated hydrocarbons (methylene chloride, dichloroethane, chloroform, carbon tetrachloride, etc.); dipolar aprotic solvents (N,N-dimethylformamide, dimethylsulfoxide, sulfolane, etc.).

Preferred inorganic bases are: hydroxides, carbonates of alkaline or earth-alkaline metals (sodium, potassium, calcium, etc.).

Preferred organic bases are: pyridine, dimethylaminopyridine, aliphatic amines, (diethylamine, triethylamine, etc.), cyclic amines (morpholine, piperidine, diazabicycloundecene, etc.); alcoholates of alkaline metals (potassium t-butylate, etc.).

Preferred inorganic acids are: hydrochloric acid, sulfuric acid, etc.

Preferred organic acids are: acetic acid, citric acid, etc.

The nitrites having general formula (VII) and the carboxylic derivatives having general formula (VIII), when they are not known as such, can be prepared by means of the methods known in literature, for example, according to what is described in Journal American Chemical Society (1943), vol. 65, page 1459.

The compounds having general formula (I) have a particularly high fungicidal activity against phytopathogenic fungi which attack vines, sugar beet, cereals, vegetables, rice, Cucurbitaceae, fruit trees.

Examples of phytopathogenic fungi which can be effectively fought with the compounds having general formula (I) are:

*Helminthosporium* spp. on cereals;
*Erysiphe* spp. on cereals;
*Puccinia* spp. on cereals;
*Plasnopara viticola* on vines;
*Pythium* spp. on vegetables;
*Phytophthora* spp. on vegetables;
*Rhynchosporium* on cereals;
*Septoria* spp. on cereals;
*Sphaerotheca fuliginea* on Cucurbitaceae (for example cucumbers);
*Podosphaera leucotricha* on apple-trees;
*Pyricularia oryzae* on rice;
*Uncinula necator* on vines;
*Venturia* spp. on fruit trees;
*Botrytis cinerea* on vines and vegetables;
*Fusarium* spp. on cereals;
*Alternaria* spp. on fruit trees and vegetables;
*Cercospora* spp. on sugar beet.

The compounds having general formula (I) are capable of exerting a fungicidal action of both a curative and preventive nature and have a low or non-existing phytotoxicity.

Many groups of the compounds having general formula (I) also have a collateral insecticidal and acaricidal activity.

An object of the present invention therefore also relates to the use of the compounds having general formula (I) as insecticides and/or acaricides.

A further object of the present invention consequently relates to a method for the control of phytopathogenic fungi in agricultural crops by the application of the compounds having general formula (I).

The quantity of compound to be applied to obtain the desired effect can vary in relation to various factors such as, for example, the compound used, the crop to be preserved, the type of pathogen, the degree of infection, the climatic conditions, the method of application, the formulation adopted.

Doses of compound ranging from 10 g to 5 kg per hectare generally provide a sufficient control.

For practical uses in agriculture it is often useful to adopt fungicidal compositions containing one or more compounds having general formula (I).

The application of these compositions or compounds having formula (I) can be effected on any part of the plant, for example on the leaves, stems, branches and roots, or on the seeds themselves before sowing, or on the ground in which the plant grows.

Compositions can be used in the form of dry powders, wettable powders, emulsifiable concentrates, micro-emulsions, pastes, granulates, solutions, suspensions, etc.: the choice of the type of composition will depend on the specific use.

The compositions are prepared in the known way, for example by diluting or dissolving the active substance with a solvent medium and/or a solid diluent, optionally in the presence of surface-active agents.

Solid diluents, or carriers which can be used, are, for example: silica, kaolin, bentonite, talc, fossil flour, dolomite, calcium carbonate, magnesia, chalk, clays, synthetic silicates, attapulgite, seppiolite.

Liquid diluents which can be used are, for example, in addition to water, aromatic organic solvents (xylols or alkyl benzene mixtures, chlorobenzene, etc.), paraffins (oil fractions), alcohols (methanol, propanol, butanol, octanol, glycerine, etc.), esters (ethyl acetate, isobutyl acetate etc.), ketones (cyclohexanone, acetone, acetophenone, isophorone, ethylamylketone, etc.), amides (N,N-dimethylformamide, N-methylpyrrolidone, etc.).

Surface-active agents which can be used are salts of sodium, calcium, triethylamines or triethanolamines, alkylsulfonates, alkylarylsulfonates, polyethoxylated alkylphenols, polyethoxylated esters of sorbitol, ligninsulfonates, etc.

The compositions can also contain special additives for particular purposes, for example adhesion agents such as arabic rubber, polyvinyl alcohol, polyvinylpyrrolidone, etc.

If desired, it is possible to add other active principles to the compositions, compatible with the compounds having general formula (I), such as for example other fungicides, phytoregulators, antibiotics, herbicides, insecticides, fertilizers.

Examples of other fungicides which can be included in the compositions of the invention are:

AC-382042, acibenzolar, ampropylphos, anilazine, azaconazole, azoxystrobin, benalaxyl (in its racemic form or as an optically active R isomer), benclothiaz, benomyl, bitertanol, blasticidin-S, bromuconazole, bupirimate, buthiobate, captafol, captan, carbendazim, carboxin, carpropamid, chinomethionat, chloroneb, chlorothalonil, chlozolinate, cyazofamid, cymoxanil, cyproconazole, cyprodinil, debacarb, dichlofluanid, dichlone, dichlobutrazol, dichlomezine, dichloran, dicyclomet, diethofencarb, diphenoconazole, diflumetorim, dimethirimol, dimethomorph, diniconazole, dinocap, a fungicide dipeptide, dipyrithione, ditalimphos, dithianon, dodemorph, dodine, edifenphos, epoxiconazole, etaconazole, ethaboxam, ethirimol, ethoxyquin, etridiazole, famoxadone, fenamidone, fenaminosulf, fenapanyl, fenarimol, fenbuconazole, fenfuram, fenhexamid, fenpiclonyl, fenpropidin, fenpropimorph, fentin, ferbam, ferimzone, fluazinam, fludioxonyl, flumetover, flumorph, fluoroimide, fluotrimazole, fluoxastrobin, fluquinconazole, flusilazole, flusulfamide, flutolanil, flutriafol, folpet, fosetylaluminium, fuberidazole, furalaxyl, furconazole; guazatine, hexaconazole, hydroxyquinoline sulfate, hymexazol, ICIA0858, imazalil, imibenconazole, iminoctadine, ipconazole, iprobenphos, iprodione, isoprothiolane, iprovalicarb, kasugamycin, kresoxim-methyl, mancopper, mancozeb, maneb, mebenil, mepanipyrim, mepronil, metalaxyl, metalaxyl-M, metconazole, methfuroxam, metiram, metsulfovax, MON-65500, myclobutanil, natamycin, nitrothal-isopropyl, nuarimol, ofurace, orisastrobin, oxadixyl, oxycarboxin, pefurazoate, penconazole, pencycuron, pentachlorophenol and its salts, phthalide, piperalin, Bordeaux mixture, polyoxins, probenazole, prochloraz, procymidone, propamocarb, propiconazole, propineb, proquinazid, prothiocarb, prothioconazole, pycoxystrobin, pyracarbolid, pyrachlostrobin, pyrazophos, pyrifenox, pyrimethanil, pyroquilon, pyroxyfur, quinacetol, quinazamid, quinconazole, quinoxyfen, quintozene, rabenazole, cuprum hydroxyde, cuprum oxychloride, cuprum sulfate, RH-7281, RPA-407213, simeconazole, spiroxamine, spiromesifen, SSF-126 (metominostrobin), streptomycin, SYP-L-190, tebuconazole, tetraconazole, thiabendazole, thicyofen, thifluzamide, thiophanatemethyl, thiram, tioxymid, tolclofos-methyl, tolylfluanid, triadimefon, triadimenol, triarimol, triazbutil, triazoxide, tricyclazole, tridemorf, trifloxystrobin (CGA 279202), triflumizole, triforine, triticonazole, validamycin, vinclozolin, zineb, ziram, sulfur, zoxamide.

These fungicidal compounds are commercial compounds or compounds about to be commercialized. Their description can be easily found in technical literature, for example in "The pesticide manual", 2000, XII edition, British Crop Protection Council Ed.

Dipeptide with a fungicidal activity refers to one of the compounds among those claimed in patent application EP-A-1028125.

The concentration of active principle in the above compositions can vary within a wide range depending on the active compound, the applications for which they are destined, the environmental conditions and type of formulation adopted.

The concentration of active principle generally ranges from 1% to 90%, preferably from 5 to 50%.

The following examples are provided as an illustration of the present invention, but should in no way be considered as limiting the scope of the invention itself.

EXAMPLE 1

Preparation of methyl (E)-3-methoxy-2-{2-[2-(trifluoromethyl)-5-methylthiazol-4-yloxymethyl]-phenyl}acrylate. (Compound Nr.1)

A solution of methyl (E)-3-methoxy-2-(2-bromomethylphenyl)acrylate (19.8 g) in N,N-dimethylformamide (50 ml) is added at room temperature to a solution of 2-(trifluoromethyl)-4-hydroxy-5-methylthiazole (14.1 g) in N,N-dimethylformamide (50 ml) containing potassium carbonate (10.6 g).

After stirring overnight, the reaction mixture is diluted with water (200 ml) and extracted with ethyl acetate (100 ml×2 times).

The organic phases are joined, washed with water (100 ml×3 times), anhydrified with sodium sulfate and concentrated at reduced pressure.

The raw product obtained is purified by chromatography on silica gel eluating with hexane/ethyl acetate 19/1.

23 g of the desired product are obtained.

M.p.=59° C.

$^1$H-NMR(δ-ppm, CDCl$_3$)=2.25 (s, 3H); 3.15 (s, 3H); 3.3 (s 3H); 5.25 (s, 2H); 7.1–7.6 (m, 5H). GC-MS: 387(M$^+$).

EXAMPLE 2

Preparation of methyl (E)-3-methoxy-2-[2-(2-(pyridin-2-yl)-5-methylthiazol-4-yloxymethyl)phenyl]-acrylate. (Compound Nr. 2)

A solution of 2-(pyridin-2-yl)-4-hydroxy-5-methylthiazole (0.77 g) in N,N-dimethylformamide (5 ml) is added dropwise to a suspension of sodium hydride (0.16 g) in N,N-dimethylformamide (5 ml).

After 30', a solution of methyl (E)-3-methoxy-2-(2-bromomethylphenyl)acrylate (1.5 g) in N,N-dimethylformamide (5 ml) is added to the reaction mixture, maintained under stirring and at room temperature.

After 4 hours at room temperature, the mixture is diluted with water (20 ml) and extracted with ethyl acetate (20 ml×2 times). The organic phases are joined, anhydrified with sodium sulfate and concentrated at reduced pressure. The raw product obtained is purifed by chromatography on silica gel eluating with hexane/ethyl acetate 9/1. 1.3 g of the desired product are obtained.

$^1$H-NMR (δ-ppm, CDCl$_3$)=2.3 (s, 3H); 3.7 (s, 3H); 3.9 (s, 3H); 5.3(s, 2H); 7–7.8(m, 7H); 8.1(dd, 1H); 8.6(dd, 1H).

EXAMPLE 3

Preparation of methyl (E)-2-methoxyimino-2-[2-(2-(pyridin-2-yl)-5-methylthiazol-4-yloxymethyl)-phenyl]acetate. (Compound Nr. 3)

A solution of 2-(pyridin-2-yl)-4-hydroxy-5-methylthiazole (1.55 g) in N,N-dimethylformamide (10 ml) is added dropwise to a suspension of sodium hydride (0.32 g) in N,N-dimethylformamide (12 ml).

After 30', a solution of methyl (E)-2-methoxyimino-2-(2-bromomethylphenyl)acetate (3.1 g) in N,N-dimethylformamide (15 ml) is added to the reaction mixture, maintained under stirring and at room temperature.

After 4 hours at room temperature, the mixture is diluted with water (20 ml) and extracted with ethyl acetate (20 ml×2 times). The organic phases are joined, anhydrified with sodium sulfate and concentrated at reduced pressure. The raw product obtained is purified by chromatography on silica gel eluating with hexane/ethyl acetate 9/1. 2.9 g of the desired product are obtained.

$^1$H-NMR (δ-ppm, CDCl$_3$)=2.3 (s, 3H); 3.8 (s, 3H); 3.95 (s, 3H); 5.3(s, 2H); 7–7.8(m, 6H); 8.1(dd, 1H); 8.6(dd, 1H).

EXAMPLE 4

Preparation of N-methyl-(E)-2-methoxyimino-2-[2-(2-(pyridin-2-yl)-5-methylthiazol-4-yloxymethyl)phenyl]acetamide. (Compound Nr. 4)

An aqueous solution at 40% of N-methylamine (1.2 ml) is added to a solution of methyl (E)-2-methoxyimino-2-[2-(2-(pyridin-2-yl)-5-methylthiazol-4-yloxymethyl)phenyl] acetate (Compound Nr. 3; 1.5 g) in N,N-dimethylformamide and methanol in a ratio of 1:2 (9 ml). The mixture is left under stirring for 2 hours at room temperature, diluted with water and extracted with ethyl acetate (20 ml×2). The organic phases are joined, washed with water (30 ml×2), anhydrified with sodium sulfate and concentrated at reduced pressure. 1.4 g of raw product are obtained, which does not require further purification.

$^1$H-NMR (δ-ppm, CDCl$_3$)=2.3 (s, 3H); 3.45 (d, 3H); 3.85 (s, 3H); 5.3(s, 2H); 7–7.8(m, 6H); 8.1(dd, 1H); 8.6(dd, 1H).

Operating analogously to what is described in the previous examples, the compounds indicated in Table 1 below, were prepared.

TABLE 1

| Comp. Nr | R$_1$ | R$_2$ | R$_3$ | R$_4$ | R$_5$ | Y | Z |
|---|---|---|---|---|---|---|---|
| 5 | CF$_3$ | CH$_3$ | Me | Me | H | O | N |
| 6 | CF$_3$ | CH$_3$ | Me | Me | H | NH | N |
| 7 | CF$_3$CF$_2$ | CH$_3$ | Me | Me | H | O | CH |
| 8 | CF$_3$CF$_2$ | CH$_3$ | Me | Me | H | NH | N |
| 9 | CF$_2$HCF$_2$ | CH$_3$ | Me | Me | H | O | CH |
| 10 | CF$_3$CF$_2$ | CH$_3$ | Me | Me | H | O | N |
| 11 | CF$_3$CFH | CH$_3$ | Me | Me | H | O | CH |
| 12 | CF$_2$HCF$_2$ | CH$_3$ | Me | Me | H | NH | N |
| 13 | CF$_3$CH$_2$ | CH$_3$ | Me | Me | H | O | CH |
| 14 | CF$_2$HCF$_2$ | CH$_3$ | Me | Me | H | O | N |
| 15 | CF$_3$CFH | CH$_3$ | Me | Me | H | NH | N |
| 16 | CF$_3$ | H | Me | Me | H | O | CH |
| 17 | CF$_3$ | H | Me | Me | H | NH | N |
| 18 | CF$_3$ | H | Me | Me | H | O | N |
| 19 | CF$_3$ | Cl | Me | Me | H | O | CH |
| 20 | CF$_3$ | Cl | Me | Me | H | NH | N |
| 21 | CF$_3$ | Cl | Me | Me | H | O | N |
| 22 | CF$_3$CH$_2$ | CH$_3$ | Me | Me | H | NH | N |
| 23 | CF$_3$ | CH$_3$CH$_2$ | Me | Me | H | NH | N |
| 24 | CF$_3$CFH | CH$_3$ | Me | Me | H | O | N |
| 25 | CF$_3$CH$_2$ | CH$_3$ | Me | Me | H | O | N |
| 26 | CF$_3$ | CH$_3$CH$_2$ | Me | Me | H | O | CH |
| 27 | CF$_3$ | Cyclopropyl | Me | Me | H | O | CH |
| 28 | CF$_3$ | CH$_3$ | Me | Me | 6-Cl | O | CH |
| 29 | CF$_3$ | CH$_3$ | Me | Me | 6-Cl | NH | N |
| 30 | CF$_3$ | CH$_3$ | Me | Me | 6-F | O | CH |
| 31 | CF$_3$ | CH$_3$ | Me | Me | 6-F | NH | N |
| 32 | CF$_2$H | CH$_3$ | Me | Me | H | O | CH |
| 33 | CF$_2$H | CH$_3$ | Me | Me | H | NH | N |
| 34 | CF$_2$Cl | CH$_3$ | Me | Me | H | O | CH |
| 35 | CF$_2$Cl | CH$_3$ | Me | Me | H | NH | N |
| 36 | CF$_3$ | F | Me | Me | H | O | CH |
| 37 | CF$_3$ | CH$_3$ | Me | Me | 6-CH$_3$ | O | CH |
| 38 | CF$_3$ | phenyl | Me | Me | H | O | CH |
| 39 | CF$_3$ | 2-pyridyl | Me | Me | H | O | CH |
| 40 | Phenyl | Me | Me | Me | H | O | CH |
| 41 | Phenyl | Me | Me | Me | H | O | N |
| 42 | Phenyl | Me | Me | Me | H | NH | N |
| 43 | 4-Cl-Phenyl | Me | Me | Me | H | O | CH |
| 44 | 4-Cl-Phenyl | Me | Me | Me | H | O | N |
| 45 | 4-Cl-Phenyl | Me | Me | Me | H | NH | N |
| 46 | 2-F-Phenyl | Me | Me | Me | H | O | CH |
| 47 | 2-F-Phenyl | Me | Me | Me | H | O | N |
| 48 | 2-F-Phenyl | Me | Me | Me | H | NH | N |
| 49 | 3-Me-pyridin-2-yl | Me | Me | Me | H | O | CH |
| 50 | 3-Me-pyridin-2-yl | Me | Me | Me | H | O | N |
| 51 | 3-Me-pyridin-2-yl | Me | Me | Me | H | NH | N |
| 52 | Pyridin-2-yl | H | Me | Me | H | O | CH |
| 53 | Pyridin-2-yl | H | Me | Me | H | O | N |
| 54 | Pyridin-2-yl | H | Me | Me | H | NH | N |
| 55 | Pyridin-2-yl | CF$_3$ | Me | Me | H | O | CH |
| 56 | Pyridin-2-yl | CF$_3$ | Me | Me | H | O | N |
| 57 | Pyridin-2-yl | CF$_3$ | Me | Me | H | NH | N |
| 58 | Pyridin-2-yl | Cl | Me | Me | H | O | CH |
| 59 | Pyridin-2-yl | Cl | Me | Me | H | O | N |
| 60 | Pyridin-2-yl | Cl | Me | Me | H | NH | N |
| 61 | Pyridin-2-yl | COOMe | Me | Me | H | O | CH |
| 62 | Pyridin-2-yl | COOMe | Me | Me | H | O | N |
| 63 | Pyridin-2-yl | COOMe | Me | Me | H | NH | N |
| 64 | Phenyl | COOMe | Me | Me | H | O | CH |
| 65 | Phenyl | COOMe | Me | Me | H | O | N |
| 66 | Phenyl | COOMe | Me | Me | H | NH | N |
| 67 | Me | Me | Me | Me | H | O | CH |
| 68 | Me | Me | Me | Me | H | O | N |
| 69 | Me | Me | Me | Me | H | NH | N |
| 70 | Isopropyl | Me | Me | Me | H | O | CH |
| 71 | Isopropyl | Me | Me | Me | H | O | N |
| 72 | Isopropyl | Me | Me | Me | H | NH | N |
| 73 | Cyclopropyl | Me | Me | Me | H | O | CH |
| 74 | Cyclopropyl | Me | Me | Me | H | O | N |
| 75 | Cyclopropyl | Me | Me | Me | H | NH | N |
| 76 | Cyclohexyl | H | Me | Me | H | O | CH |
| 77 | Cyclohexyl | H | Me | Me | H | O | N |
| 78 | Cyclohexyl | H | Me | Me | H | NH | N |
| 79 | CH$_2$cyclopropyl | Me | Me | Me | H | O | CH |
| 80 | CH$_2$cyclopropyl | Me | Me | Me | H | O | N |
| 81 | CH$_2$cyclopropyl | Me | Me | Me | H | NH | N |
| 82 | Phenyl | Me | Me | Me | 6-Cl | O | CH |
| 83 | Phenyl | Me | Me | Me | 6-Cl | O | N |
| 84 | Phenyl | Me | Me | Me | 6-Cl | NH | N |
| 85 | Phenyl | Me | Me | Me | 6-F | O | CH |
| 86 | Phenyl | Me | Me | Me | 6-F | O | N |
| 87 | Phenyl | Me | Me | Me | 6-F | NH | N |
| 88 | Pyrazinyl | Me | Me | Me | H | O | CH |
| 89 | Pyrazinyl | Me | Me | Me | H | O | N |
| 90 | Pyrazinyl | Me | Me | Me | H | NH | N |
| 91 | Pyridin-3-yl | Me | Me | Me | H | O | CH |
| 92 | Pyridin-3-yl | Me | Me | Me | H | O | N |
| 93 | Pyridin-3-yl | Me | Me | Me | H | NH | N |
| 94 | Pyridin-4-yl | Me | Me | Me | H | O | CH |
| 95 | Pyridin-4-yl | Me | Me | Me | H | O | N |
| 96 | Pyridin-4-yl | Me | Me | Me | H | NH | N |
| 97 | 2-Cl-pyridin-3-yl | Me | Me | Me | H | O | CH |
| 98 | 2-Cl-pyridin-3-yl | Me | Me | Me | H | O | N |
| 99 | 2-Cl-pyridin-3-yl | Me | Me | Me | H | NH | N |
| 100 | 4-CF$_3$-pyridin-3-yl | Et | Me | Me | H | O | CH |
| 101 | 4-CF$_3$-pyridin-3-yl | Et | Me | Me | H | O | N |
| 102 | 4-CF$_3$-pyridin-3-yl | Et | Me | Me | H | NH | N |
| 103 | Pyridin-2-yl | COMe | Me | Me | H | O | CH |
| 104 | Pyridin-2-yl | COMe | Me | Me | H | O | N |
| 105 | Pyridin-2-yl | COMe | Me | Me | H | NH | N |
| 106 | Phenyl | CON(Me)$_2$ | Me | Me | H | O | CH |
| 107 | Phenyl | CON(Me)$_2$ | Me | Me | H | O | N |
| 108 | Phenyl | CON(Me)$_2$ | Me | Me | H | NH | N |
| 109 | Me | Phenyl | Me | Me | H | O | CH |
| 110 | Me | Phenyl | Me | Me | H | O | N |
| 111 | Me | Phenyl | Me | Me | H | NH | N |
| 112 | Et | Cyclopentyl | Me | Me | H | O | CH |
| 113 | Et | Cyclopentyl | Me | Me | H | O | N |
| 114 | Et | Cyclopentyl | Me | Me | H | NH | N |
| 115 | 4-Me-phenyl | CN | Me | Me | H | O | CH |
| 116 | 4-Me-phenyl | CN | Me | Me | H | O | N |
| 117 | 4-Me-phenyl | CN | Me | Me | H | NH | N |
| 118 | 2,4-diCl-phenyl | Ome | Me | Me | H | O | CH |
| 119 | 2,4-diCl-phenyl | Ome | Me | Me | H | O | N |
| 120 | 2,4-diCl-phenyl | Ome | Me | Me | H | NH | N |
| 121 | 4-CF$_3$-phenyl | cyclopropyl | Me | Me | H | O | CH |
| 122 | 4-CF$_3$-phenyl | cyclopropyl | Me | Me | H | O | N |
| 123 | 4-CF$_3$-phenyl | cyclopropyl | Me | Me | H | NH | N |
| 124 | 2,6-diF-phenyl | H | Me | Me | 3-Cl | O | CH |
| 125 | 2,6-diF-phenyl | H | Me | Me | 3-Cl | O | N |
| 126 | 2,6-diF-phenyl | H | Me | Me | 3-Cl | NH | N |
| 127 | 2-thienyl | Me | Me | Me | H | O | CH |
| 128 | Cl | Me | Me | Me | H | O | CH |
| 129 | Br | Me | Me | Me | H | O | CH |

EXAMPLE 5

Preparation of 2-(trifluoromethyl)-4-hydroxy-5-methylthiazole. (Reaction scheme B; compound (III')-1)

A solution of trifluorothioacetamide (35.5 g) in N,N-dimethylformamide (60 ml) is added dropwise to a suspension of sodium hydride at 60% (11 g) in N,N-dimethylformamide (60 ml), the temperature being maintained at −10° C.

At the end of the addition, the reaction mixture is kept under stirring at −10° C. for about 20', and a solution of methyl 2-bromopropionate (27.6 ml) in N,N-dimehylformamide (60 ml) is then added dropwise.

After 45' at a temperature ranging from −10° C. to −5° C., the reaction mixture is diluted with acid water (200 ml), bringing the pH to about 6, and extracted with ethyl acetate (100 ml×2 times).

The organic phases are joined, washed with water (100 ml×3 times), anhydrified with sodium sulfate and concentrated at reduced pressure.

The raw product obtained is purified by chromatography on silica gel eluating with hexane/ethyil acetate 99/1.

25 g of the desired product are obtained.

M.p.=108–110° C. $^1$H-NMR(δ-ppm, DMSO)=2.3 (s, 3H); 10.4 (s, 1H). GC-MS: 183(M$^+$).

Elemental analysis [% found (theoretical)]=C 32.85 (32.79); H 2.10.(2.18); N 7.45 (7.65).

EXAMPLE 6

Preparation of 2-(trifluoromethyl)-4-hydroxy-5-methylthiazole. (Reaction scheme C; compound (III')-1)

Trifluoroacetonitrile (11.8 g) is condensed in a solution of thiolactic acid (13.1 g) and pyridine (2.5 ml) in tetrahydrofuran (120 ml) mantained at −70° C. and the mixture is kept under stirring at this temperature for about an hour.

The reaction mixture is gradually brought to room temperature and is then heated to reflux temperature for an hour.

It is cooled, the solvent is evaporated, water is added (50 ml) to the reaction raw product and the mixture is extracted with ethyl acetate (50 ml×2 times).

The organic phases are joined, anhydrified with sodium sulfate and concentrated at reduced pressure.

The raw product obtained is purified by chromatography on silica gel eluating with hexane/ethyl acetate 99/1.

15.5 g of the desired product are obtained.

M.p.=108–110° C.

$^1$H-NMR(δ-ppm, DMSO)=2.3 (s, 3H); 10.4 (s, 1H). GC-MS: 183 (M$^+$).

Elemental analysis [% found (theoretical)]=C 31.95 (32.79); H 2.02.(2.18); N 7.93 (7.65).

EXAMPLE 7

Preparation of 2-(pyridin-2-yl)-4-hydroxy-5-methylthiazole. (Reaction scheme C).

1.9 g of pyridine are added dropwise to a mixture of thiolactic acid (10.2 g) and 2-cyanopyridine (10 g), and the mixture is heated to 100° C. for 2 hours.

After cooling, ethanol is added and the precipitate formed is filtered; the solid is recrystallized from ethyl ether and dried. 15.5 g of product are obtained.

$^1$H-NMR (δ-ppm, DMSO-d$_6$): 2.25 (s, 3H); 7.35–7.6 (m, 2H); 8.05–8.35 (m, 2H); 10.5 (bs, 1H).

Operating analogously to what is described in the previous examples, the intermediates indicated in Table 2 below, were prepared

TABLE 2

| Compound Nr | R$_1$ | R$_2$ |
|---|---|---|
| (III')-3 | CF$_3$ | H |
| (III')-4 | CF$_2$H | Me |
| (III')-5 | CF$_3$ | Cl |
| (III')-6 | CF$_3$ | Et |

TABLE 2-continued

| Compound Nr | R$_1$ | R$_2$ |
|---|---|---|
| (III')-7 | CF$_3$ | Cyclopropyl |
| (III')-8 | CF$_3$ | Phenyl |
| (III')-9 | CF$_3$ | 4-chlorophenyl |
| (III')-10 | CF$_3$ | 4-methoxyphenyl |
| (III')-11 | CF$_3$ | 4-methylphenyl |
| (III')-12 | CF$_3$ | 2,4-dichlorophenyl |
| (III')-13 | CF$_3$ | 2-pyridyl |
| (III')-14 | CF$_3$ | Isopropyl |
| (III')-15 | CF$_3$ | 2-pyrimidyl |
| (III')-16 | CF$_3$ | 2-furyl |
| (III')-17 | CF$_3$ | Ethoxycarbonyl |
| (III')-18 | CF$_3$ | CN |
| (III')-19 | CF$_3$CF$_2$ | Me |
| (III')-20 | CF$_3$CF$_2$ | H |
| (III')-21 | CF$_3$CF$_2$ | Phenyl |
| (III')-22 | CF$_3$CF$_2$ | Cyclopropyl |
| (III')-23 | CF$_3$CF$_2$ | 4-chlorophenyl |
| (III')-24 | CF$_3$CF$_2$ | 2-pyridyl |
| (III')-25 | CF$_3$CF$_2$ | Cl |
| (III')-26 | CF$_3$CHF | Me |
| (III')-27 | CF$_3$CHF | H |
| (III')-28 | CF$_3$CHF | Phenyl |
| (III')-29 | CF$_3$CHF | Isopropyl |
| (III')-30 | CF$_3$CHF | 4-methylphenyl |
| (III')-31 | CF$_3$CHF | 2,4-dichlorophenyl |
| (III')-32 | CF$_2$HCF$_2$ | Me |
| (III')-33 | CF$_2$HCF$_2$ | H |
| (III')-34 | CF$_2$HCF$_2$ | Phenyl |
| (III')-35 | CF$_2$HCF$_2$ | Ethyl |
| (III')-36 | CF$_2$HCF$_2$ | 2-pyridyl |
| (III')-37 | CF$_2$HCF$_2$ | Cyclopentyl |
| (III')-38 | CF$_3$CH$_2$ | Me |
| (III')-39 | CF$_3$CH$_2$ | H |
| (III')-40 | CF$_3$CH$_2$ | Phenyl |
| (III')-41 | CF$_3$CH$_2$ | Cl |
| (III')-42 | CF$_3$CH$_2$ | 4-chlorophenyl |
| (III')-43 | CF$_3$CH$_2$ | 4-methoxyphenyl |
| (III')-44 | CF$_3$CH$_2$ | Cyclopropyl |
| (III')-45 | CF$_2$H | H |
| (III')-46 | CF$_2$H | Phenyl |
| (III')-47 | CF$_2$H | Cl |
| (III')-48 | CF$_2$H | Cyclopentyl |
| (III')-49 | CF$_2$H | 4-chlorophenyl |
| (III')-50 | CF$_2$H | 4-methylphenyl |
| (III')-51 | CF$_2$Cl | Me |
| (III')-52 | CF$_2$Cl | H |
| (III')-53 | CF$_2$Cl | Phenyl |
| (III')-54 | CF$_2$Cl | 4-chlorophenyl |
| (III')-55 | CF$_2$Cl | Cyclopropyl |
| (III')-56 | CF$_2$Cl | 2-pyridyl |

EXAMPLE 8

Determination of the fungicidal activity against vine mildew (*Plasmopara viticola*).

Leaves of vines (cultivar Dolcetto), cultivated in vases in a conditioned environment (20±1° C., 70% relative humidity) are treated by spraying both sides of the leaves with compounds 1, 2 and 3, dispersed in a hydroacetone solution at 20% by volume of acetone.

After remaining 24 hours in a conditioned environment, the plants are sprayed on both sides of the leaves with an aqueous suspension of conidia of *Plasmopara viticola* (20000 conidia per cm$^3$).

The plants are kept in a humidity saturated environment at 21° C. for the incubation period of the fungus.

At the end of this period (7 days), the fungicidal activity is evaluated according to a percentage evaluation scale from 0 (completely infected plant) to 100 (healthy plant).

All the compounds tested showed a fungus control of over 90 at a concentration of 1000 ppm.

EXAMPLE 9

Determination of the fungicidal activity against wheat powdery mildew (*Erysiphe graminis*).

Leaves of wheat plants (cultivar Gemini), cultivated in vases in a conditioned environment (20±1° C., 70% relative humidity) are treated by spraying both sides of the leaves with compounds 1, 2 and 3, dispersed in a hydroacetone solution at 20% by volume of acetone.

After remaining 24 hours in a conditioned environment, the plants are sprayed on both sides of the leaves with an aqueous suspension of conidia of *Erysiphe graminis* (200000 conidia per cm$^3$)

The plants are kept in a humidity saturated environment at a temperature ranging from 18 to 24° C. for the incubation period of the fungus.

At the end of this period (12 days), the fungicidal activity is evaluated according to a percentage evaluation scale from 0 (completely infected plant) to 100 (healthy plant).

All the compounds tested showed a fungus control of over 90 at a concentration of 1000 ppm.

EXAMPLE 10

Determination of the fungicidal activity against wheat rust (*Puccinia recondita*).

Leaves of wheat plants (cultivar Gemini), cultivated in vases in a conditioned environment (20±1° C., 70% relative humidity) are treated by spraying both sides of the leaves with compounds 1, 2 and 3, dispersed in a hydroacetone solution at 20% by volume of acetone.

After remaining 24 hours in a conditioned environment, the plants are sprayed on both sides of the leaves with an aqueous suspension of conidia of *Puccinia recondita* (200000 conidia per cm$^3$).

The plants are kept in a humidity saturated environment at a temperature ranging from 18 to 24° C. for the incubation period of the fungus.

At the end of this period (14 days), the fungicidal activity is evaluated according to a percentage evaluation scale from 0 (completely infected plant) to 100 (healthy plant).

All the compounds tested showed a fungus control of over 90 at a concentration of 1000 ppm.

We claim:

1. A compound having general formula (I):

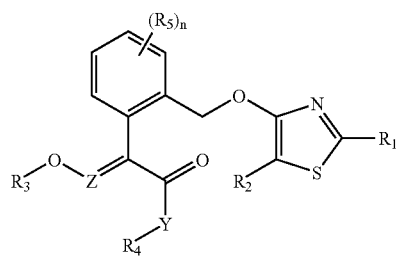

wherein:

$R_1$ represents a hydrogen atom; a linear or branched $C_1$–$C_6$ alkyl or haloalkyl group, optionally substituted; a $C_2$–$C_6$ alkenyl or haloalkenyl group, optionally substituted; a $C_2$–$C_6$ alkynyl or haloalkynyl group, optionally substituted; a $C_3$–$C_6$ cycloalkyl group, optionally substituted; an aryl group, optionally substituted; a heteroaryl group, optionally substituted; a heterocyclic group, optionally substituted; a halogen atom;

$R_2$ represents a hydrogen atom; a halogen atom selected from chlorine, fluorine, bromine or iodine; a linear or branched $C_1$–$C_6$ alkyl or haloalkyl group, optionally substituted; a linear or branched $C_2$–$C_6$ alkenyl or haloalkenyl group, optionally substituted; a linear or branched $C_2$–$C_6$ alkynyl or haloalkynyl group, optionally substituted; a $C_3$–$C_6$ cycloalkyl group, optionally substituted; a linear or branched $C_1$–$C_6$ alkoxy or haloalkoxy group, optionally substituted; a linear or branched $C_1$–$C_6$ alkylthio or haloalkylthio group, optionally substituted; a $C_3$–$C_6$ cycloalkoxy group, optionally substituted; a cyano group; a linear or branched $C_2$–$C_8$ alkoxycarbonyl group, optionally substituted; an aminocarbonyl group; a linear or branched $C_2$–$C_8$ alkylaminocarbonyl group; a linear or branched $C_3$–$C_{15}$ dialkylaminocarbonyl group; a linear or branched $C_2$–$C_8$ alkylcarbonyl group, optionally substituted; an aryl group, optionally substituted or a heteroaryl group, optionally substituted; a heterocyclic group, optionally substituted;

$R_3$ and $R_4$ independently represent a linear or branched $C_1$–$C_4$ alkyl group;

$R_5$, the same or different when n is greater than or equal to 2, represents a halogen atom, optionally selected from fluorine, chlorine, bromine or iodine; a linear or branched $C_1$–$C_6$ haloalkyl group, optionally substituted; a linear or branched $C_1$–$C_6$ alkoxy group, optionally substituted; a linear or branched $C_1$–$C_6$ haloalkoxy group, optionally substituted; a linear or branched $C_1$–$C_6$ alkylthio group, optionally substituted; a linear or branched $C_1$–$C_6$ haloalkylthio group, optionally substituted; a $C_3$–$C_6$ cycloalkyl group optionally substituted; a linear or branched $C_2$–$C_8$ alkoxycarbonyl group; a cyano group; when $R_1$ represents a linear or branched $C_1$–$C_6$ haloalkyl group, substituted by at least two halogen atoms, the same or different, i.e. a linear or branched $C_1$–$C_6$ polyhaloalkyl group, $R^5$ also represents a linear or branched $C_1$–$C_6$ alkyl group, optionally substituted;

Y represents an oxygen atom;

Z represents a CH group;

n is a number ranging from 0 to 4.

2. A compound according to claim 1, characterized in that it is an isomeric mixture in any proportion of the isomers E and Z of the compounds having formula (I).

3. A compound according to claim 1, characterized in that it is the isomer E or the isomer Z of the compounds having formula (I).

4. A compound according to claim 1, characterized in that it is the isomer E of the compounds having formula (I).

5. A compound according to claim 1 characterized in that the group $R_1$ is selected from a linear or branched $C_1$–$C_6$ alkyl or haloalkyl group, optionally substituted; a $C_3$–$C_6$ cycloalkyl group, optionally substituted; an aryl group, optionally substituted; a heteroaryl group, optionally substituted.

6. A compound according to claim 1, characterized in that the group $R_2$ is selected from a hydrogen atom; a halogen atom; a linear or branched $C_1$–$C_6$ alkyl or haloalkyl group, optionally substituted; a $C_3$–$C_6$ cycloalkyl group, optionally substituted; a linear or branched $C_2$–$C_8$ alkoxycarbonyl group, optionally substituted.

7. A compound according to claim 1, characterized in that $R_3$ and $R_4$ are equal to a methyl group.

8. A compound according to claim 1, characterized in that $R_5$ is selected from a halogen atom, a $C_1$–$C_6$ haloalkyl group or, when $R_1$ represents a $C_1$–$C_6$ polyhaloalkyl group, $R_5$ represents a linear or branched $C_1$–$C_6$ alkyl group, optionally substituted.

9. A compound according to claim 1, characterized in that n is equal to 0 or 1.

10. A compound according to claim 1, characterized in that it is selected from:
(1) methyl (E)-3-methoxy-2-{2-[2-(trifluoromethyl)-5-methyl-thiazol-4-yloxymethyl]phenyl}acrylate;
(2) methyl-(E)-3-methoxy-2-{2-[2-(1,1,2,2,2penta-fluoroethyl)-5-methylthiazol-4-yloxymethyl]-phenyl}acrylate;
(3) methyl(E)-3-methoxy-2-{2-[2-(1,1,2,2-tetra-fluoroethyl)-5-methylthiazol-4-yloxymethyl]-phenyl}acrylate;
(4) methyl(E)-3-methoxy-2-{2-[2-(1,2,2,2-tetra-fluoroethyl)-5-methylthiazol-4-yloxymethyl]-phenyl}acrylate;
(5) methyl(E)-3-methoxy-2-{2-[2-(2,2,2,-trifluoro-ethyl)-5-methylthiazol-4-yloxymethyl]phenyl}-acrylate;
(6) methyl(E)-3-methoxy-2-{2-[2-(trifluoromethyl)-thiazol-4-yloxymethyl]phenyl}acrylate;
(7) methyl(E)-3-methoxy-2-{2-[2-(trifluoromethyl)-5-chlorothiazol-4-yloxymethyl]phenyl}acrylate;
(8) methyl(E)-3-methoxy-2-{2-[2-(trifluoromethyl)-5-ethylthiazol-4-yloxymethyl]phenyl}acrylate;
(9) methyl(E)-3-methoxy-2-{2-[2-(trifluoromethyl)-5-cyclopropylthiazol-4-yloxymethyl]phenyl}acrylate;
(10) methyl(E)-3-methoxy-2-{2-[2-(difluoromethyl)-5-methylthiazol-4-yloxymethyl]phenyl}acrylate;
(11) methyl(E)-3-methoxy-2-{2-[2-(chlorodifluoro-methyl)5-methylthiazol-4-yloxymethyl]phenyl}acrylate;
(12) methyl(E)-3-methoxy-2-[2-(2-(pyridin-2-yl)-5-methylthiazol-4-yloxymethyl)phenyl]acrylate;
(13) methyl(E)-3-methoxy-2-[2-(2-(pyridin-3-yl)-5-methylthiazol-4-yloxymethyl)phenyl]acrylate;
(14) methyl(E)-3-methoxy-2-[2-(2-(pyridin-4-yl)-5-methylthiazol-4-yloxymethyl)phenyl]acrylate;
(15) methyl(E)-3-methoxy-2-[2-(2-(4-chlorophenyl)-5-methyl-thiazol-4-yloxymethyl)phenyl]acrylate;
(16) methyl(E)-3-methoxy-2-[2-((2-cyclopropyl-5-methylthiazol-4-yloxymethyl)phenyl]acrylate;
(17) methyl(E)-3-methoxy-2-[2-(2-(pyridin-2-yl)-thiazol-4-yloxymethyl)phenyl]acrylate;
(18) methyl(E)-3-methoxy-2-[2-(2-(pyridin-2-yl)-5-trifluoromethylthiazol-4-yloxymethyl)phenyl]-acrylate;
(19) methyl(E)-3-methoxy-2-[2-(2-(4-trifluoromethyl-phenyl)-5-cyclopropylthiazol-4-yloxymethyl)-phenyl]acrylate; and
(20) methyl(E)-3-methoxy-2-[2-(2-(2,4-dichloro-phenyl)-5-methoxylthiazol-4-yloxymethyl)phenyl]-acrylate.

11. A process for the preparation of the compounds having general formula (I) according to claim 1, characterized in that it comprises a condensation reaction of a compound having general formula (II) with a thiazolyl derivative having general formula (III), according to reaction scheme A:

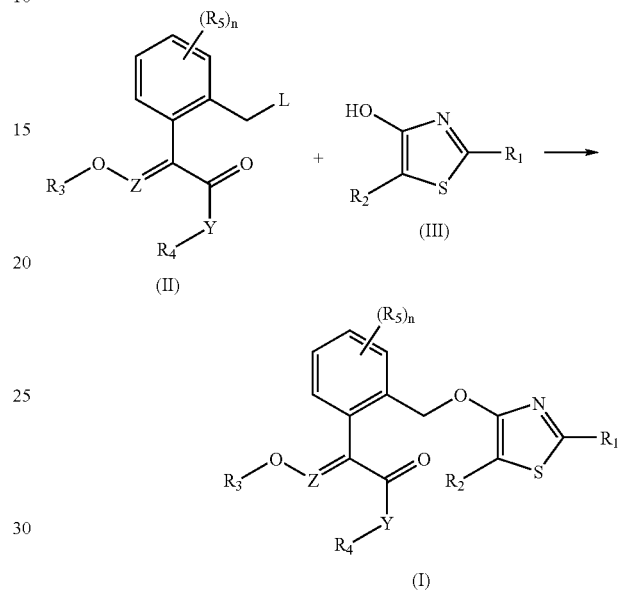

Scheme A wherein $R_1$, $R_2$, $R_3$, $R_4$, $R_5$, Y, Z and n have the meanings defined above, L represents an outgoing group such as a chlorine atom, a bromine atom, an $RSO_3^-$ group wherein R represents a $C_1$–$C_6$ alkyl or haloalkyl or a phenyl, optionally substituted.

12. The process according to claim 11, characterized in that the condensation is carried out in an inert organic solvent, at a temperature ranging from 0° C. to the boiling point of the reaction mixture, optionally in the presence of an inorganic or organic base.

13. Fungicidal compositions containing as active principle one or more of the compounds having general formula (I) according to claim 1.

* * * * *